(12) United States Patent
Salegui Echeveste et al.

(10) Patent No.: US 11,426,542 B2
(45) Date of Patent: Aug. 30, 2022

(54) NEBULISER DEVICE

(71) Applicant: Lainomedical, S.L., Donostia-San Sebastián (ES)

(72) Inventors: Juan José Salegui Echeveste, Renteria (ES); Iñaki Salegi Etxebeste, Renteria (ES)

(73) Assignee: Lainomedical, S.L., Donostia-San Sebastián (ES)

( * ) Notice: Subject to any disclaimer, the term of this patent is extended or adjusted under 35 U.S.C. 154(b) by 0 days.

(21) Appl. No.: 17/519,014

(22) Filed: Nov. 4, 2021

(65) Prior Publication Data

US 2022/0054776 A1 Feb. 24, 2022

Related U.S. Application Data

(63) Continuation of application No. 15/514,057, filed as application No. PCT/ES2014/070740 on Sep. 29, 2014, now Pat. No. 11,185,646.

(30) Foreign Application Priority Data

Sep. 26, 2014 (ES) .............................. ES201431415

(51) Int. Cl.
*A61M 15/00* (2006.01)
*A61M 11/00* (2006.01)
*B65D 83/14* (2006.01)
*B05B 7/00* (2006.01)

(52) U.S. Cl.
CPC ........ *A61M 15/0085* (2013.01); *A61M 11/00* (2013.01); *A61M 11/005* (2013.01); *A61M 15/001* (2014.02); *A61M 15/0035* (2014.02); *B65D 83/14* (2013.01); *A61M 2202/04* (2013.01); *B05B 7/0012* (2013.01)

(58) Field of Classification Search
CPC ................ A61M 11/005; A61M 11/00; A61M 15/0085; A61M 15/0035; A61M 15/001
See application file for complete search history.

(56) References Cited

U.S. PATENT DOCUMENTS

| 5,388,574 | A | 2/1995 | Ingebrethsen |
| 8,025,050 | B2 | 9/2011 | Yu et al. |
| 8,555,874 | B2 | 10/2013 | Fink et al. |
| 9,895,500 | B2 | 2/2018 | Cheng et al. |
| 2002/0157663 | A1 | 10/2002 | Blacker et al. |
| 2008/0163869 | A1 | 7/2008 | Nobutani et al. |

(Continued)

FOREIGN PATENT DOCUMENTS

| EP | 1695729 A1 | 8/2006 |
| ES | 2452935 T3 | 4/2014 |

(Continued)

*Primary Examiner* — Margaret M Luarca
*Assistant Examiner* — Cana A Gallegos
(74) *Attorney, Agent, or Firm* — The Webb Law Firm

(57) ABSTRACT

A nebuliser device with a vibrating mesh, for administering medicaments, includes a casing, a nozzle, a nebuliser and a chamber that houses a medicament. The chamber housing a medicament is a disposable capsule forming an independent body that can be extracted from the casing of the device. The disposable capsule includes a connector for attaching to the nebuliser and to the casing. The connector allow the disposable capsule to be coupled to the nebuliser device or uncoupled therefrom.

12 Claims, 5 Drawing Sheets

(56) References Cited

U.S. PATENT DOCUMENTS

| | | |
|---|---|---|
| 2008/0257338 A1 | 10/2008 | Gee-Turner |
| 2009/0293868 A1* | 12/2009 | Hetzer .............. A61M 15/0085 128/200.14 |
| 2010/0083963 A1 | 4/2010 | Wharton et al. |
| 2010/0186738 A1 | 7/2010 | Kobayashi et al. |
| 2011/0108025 A1 | 5/2011 | Fink et al. |
| 2012/0048265 A1 | 3/2012 | Smaldone |
| 2013/0150812 A1 | 6/2013 | Hunter et al. |
| 2014/0116426 A1 | 5/2014 | Mullinger et al. |
| 2014/0224815 A1 | 8/2014 | Gallem et al. |
| 2014/0336618 A1 | 11/2014 | Wilkerson et al. |
| 2015/0352301 A1 | 12/2015 | Stedman et al. |
| 2015/0375252 A1 | 12/2015 | Lee et al. |
| 2016/0101245 A1* | 4/2016 | Hoekman ......... A61M 15/0035 264/537 |

FOREIGN PATENT DOCUMENTS

| | | |
|---|---|---|
| RU | 107026 U1 | 8/2011 |
| WO | 2006083014 A1 | 8/2006 |
| WO | 2010131188 A1 | 11/2010 |
| WO | 2013155201 A2 | 10/2013 |

* cited by examiner

NEBULISER DEVICE

CROSS-REFERENCE TO RELATED APPLICATIONS

This application is a continuation of U.S. patent application Ser. No. 15/514,057, filed Mar. 24, 2017, which is the United States national phase of International Application No. PCT/ES2014/070740 filed Sep. 29, 2014, and claims priority to Spanish Patent Application No. P201431415 filed Sep. 26, 2014, the disclosures of which are hereby incorporated in their entirety by reference.

BACKGROUND OF THE INVENTION

Field of the Invention

The present invention refers to a nebuliser device with a vibrating mesh.

Nebuliser devices are used in the pharmaceutical and hospital industries for administering medicaments via inhalation, preferably through the mouth, via dispersing small liquid particles in the form of fog and expelling them through a nozzle of said nebuliser device.

Patients that are following a specific treatment where a nebuliser device is needed inhale through said nebuliser device the precise dose of the medicament they have been prescribed.

Therefore, the present invention has applications in the pharmaceutical and sanitary industries, and in general in the industry dedicated to manufacturing, distributing, selling and administering medicaments.

Description of Related Art

There are different procedures and devices in the state of the art for administering medicaments via aerosols or sprays (also known as atomisers or nebuliser devices).

One example of a nebuliser device or atomiser is described in the document with American patent number U.S. Pat. No. 8,025,050 B2, which describes a nebuliser cartridge with a geometry designed to utilise the maximum medicament possible that is contained in said cartridge.

As for the procedures for administering drugs via aerosols or sprays, one of the procedures consists of dispersing or nebulising by means of a vibrating mesh.

In this type of nebuliser devices, the aerosol is generated when the liquid medicament is pushed through the micro-holes present in a mesh made of a polymer or metal alloy, depending on each case, where said mesh oscillates at a high frequency (~180 kHz).

The advantages of this technology can be summed up as follows:
  it produces a suitable size of nebulised particles;
  easy to transport due to its pocket-size;
  it operates with conventional batteries;
  inhalation at different angles of attack with a stable nebulisation (easy to use in bed, or when holding up a child or a baby in one's arms);
  silent;
  simple mechanism triggered by pushing a single button;
  valid for a wide range of medicaments;
  minimum loss and waste of medication (around 0.1 ml).

However, in spite of the aforementioned advantages it provides, the technology of nebulisation by means of a vibrating mesh currently has some drawbacks, such as the need to clean and disinfect the nebuliser device once the medicament it contains has been inhaled. This means that it is necessary to reach the highest possible number of internal areas of the nebuliser device, including the nozzle and the chamber (storing chamber) in which the drug to be administered is introduced.

Another drawback of these devices is that both the mixture of the medication introduced in the chamber as the dose of said medication is often prepared by patients themselves at their homes, which can sometimes cause mistakes in the dosage, which results in the patient receiving an incorrect treatment.

Finally, it is also common that the design of the chamber does not contribute to providing the full dose of the medication, which also results in an inadequate or insufficient treatment.

SUMMARY OF THE INVENTION

The present invention refers to a nebuliser device of the type that comprises a vibrating mesh for nebulising a medicament contained therein, which has to be administered as an aerosol to a patient.

The nebuliser device that is the object of the invention comprises a casing, a nozzle (through which the patient inhales the medicament), a chamber that houses a medicament, and a nebuliser that comprises a vibrating mesh inside it.

The most particular feature of the nebuliser device described is that the chamber housing a medicament is a disposable capsule forming an independent body that can be extracted from the casing of the device, where said disposable capsule comprises means for attaching to the nebuliser and to the casing, so that said attachment means allow the disposable capsule to be coupled to the nebuliser device and/or uncoupled therefrom.

In a first embodiment of the nebuliser device, the aforementioned attachment means comprise a threaded coupling between the nebuliser and the disposable capsule.

Alternatively, said coupling can be done without a threaded coupling, and by means of pressure fitting. In the latter case, according to an embodiment of the device, the nebuliser comprises a hinge that connects it with the disposable capsule.

The same types of threaded coupling or pressure fitting coupling (by means of a correct fitting diameter on the end of the nozzle connecting to the nebuliser and/or the disposable capsule) are also options for valid embodiments for coupling the nozzle and the nebuliser and/or the disposable capsule.

In another embodiment, the nozzle can be coupled to the casing of the nebuliser device, according to the coupling means described above.

Alternatively, the nozzle of the nebuliser device can form an integral part of the casing of the nebuliser device.

Although in the present invention the disposable capsule is disposed after each time the nebuliser device is used, the nebuliser of the nebuliser device is preferably reusable.

The nebuliser, such as it has been described, comprises a vibrating mesh inside it for nebulising the medicament.

Additionally, in a preferred embodiment of the nebuliser device, the nebuliser also comprises a piezoelectric device that actuates the vibrating mesh. Said piezoelectric device is activated by means for activating/deactivating it that, in one of the embodiments of the nebuliser device, may consist of a button on the casing of the nebuliser device.

The disposable capsule is inserted in the casing in a removable way, either remaining completely hidden inside the casing, or partially protruding from the casing.

In addition, it should be highlighted that the medicament contained inside the disposable capsule may be formed by a single phase, liquid, or by two or more phases (liquid phases or a combination of solid and liquid phases), separated by at least one internal seal in the disposable capsule.

Similarly, the nebuliser preferably comprises a punch with a cutting edge, which, when the nebuliser is coupled to the disposable capsule of the nebuliser device, it perforates the outer seal of the disposable capsule (if it has not been removed manually) and/or at least one internal seal of said disposable capsule (in those embodiments in which the disposable capsule comprises at least one internal seal), gaining access to the medicaments contained therein, and mixing the different phases that may comprise said medicament.

Said punch preferably has a hollow geometry, which allows the medicament to flow or move inside it towards the vibrating mesh of the nebuliser, and finally outside the nebuliser device.

According to a preferred way to use the nebuliser device, the user places the nozzle of the nebuliser device in their mouth and activates the means for activating/deactivating the device (for example: a button on the casing), that activates the piezoelectric device, which in turns triggers the vibrating mesh of the nebuliser of the nebuliser device. Afterwards, the user of the nebuliser device breathes in and inhales the pulverised medicament, which goes inside their body.

The purpose of the outer seal is to seal in the medicament contained in the disposable capsule.

In those embodiments in which the disposable capsule comprises at least one internal seal, the purpose of each internal seal of the disposable capsule is to seal in the medicament contained in said disposable capsule and/or separate the different phases (solid/liquids) that may comprise said medicament.

The outer seal is located preferably on the end of the disposable capsule that connects with the nebuliser.

The geometry of said disposable capsule is preferably a vertical cone (in the shape of a funnel) on the upper part thereof and a cylinder on the lower part thereof that connects with the nebuliser, and it may comprise an L-shape that joins together the upper vertical conical part with the lower cylindrical part.

The lower cylindrical part of the disposable capsule may be in the vertical position (just like the upper conical part).

In the embodiment in which the disposable capsule comprises an L-shape between the upper conical part and the lower cylindrical part, said lower cylindrical part may be arranged in an oblique or horizontal position.

BRIEF DESCRIPTION OF THE DRAWINGS

As part of the explanation as to how the invention is embodied, the following figures have been included.

DETAILED DESCRIPTION

Figure 1:
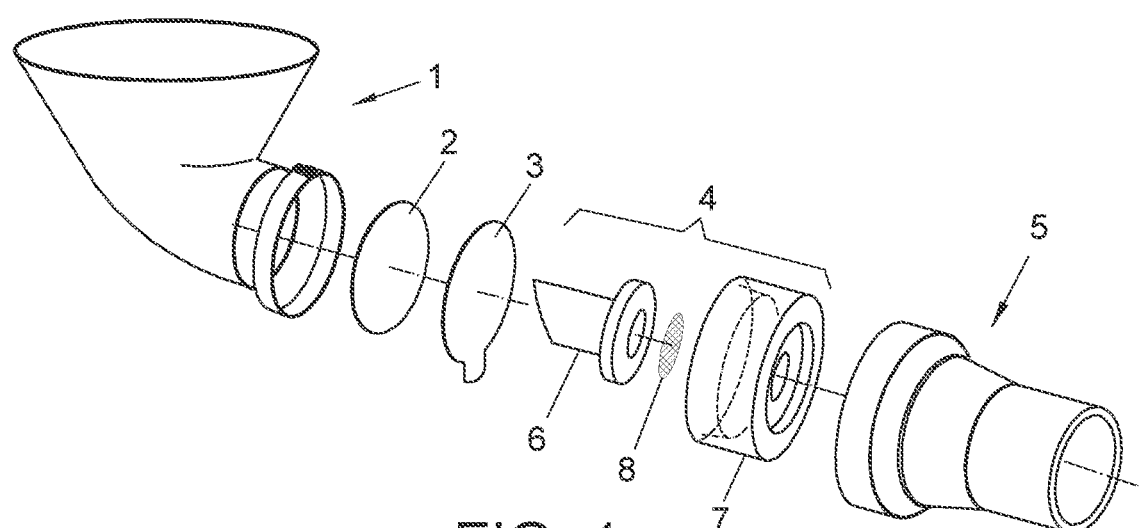
FIG. 1: Shows an exploded perspective view of a first embodiment of the nebuliser device that is the object of the invention.

The present invention, as it has been mentioned above, refers to a nebuliser device with a vibrating mesh.

The nebuliser device comprises, in any of the embodiments that are described below, a casing (10), a disposable capsule (1), a nebuliser (4) and a nozzle (5).

The nebuliser device also comprises an outer seal (3) of the disposable capsule (1), and, optionally, at least one internal seal (2) of the disposable capsule (1).

The nebuliser (4) also comprises a punch (6), a piezoelectric device (7) and a mesh (8).

In the first embodiment, the disposable capsule (1) has an L-shaped geometry with preferably a vertical cone on the upper part thereof and with a horizontal cylinder on the lower part thereof, sealed by an external seal (3).

FIG. 1 shows an exploded perspective view of the first embodiment of the nebuliser device (the casing (10) has not been represented in the drawing). Said drawing shows the key components that form part of the nebuliser device, according to the first embodiment.

A disposable capsule (1) is represented in FIG. 1, which comprises an outer seal (3) and a single internal seal (2).

In those cases where there is a single internal seal (2), this seal has the purpose of protecting the medicament contained inside the disposable capsule (1) from the environment, after the outer seal (3) has been voluntarily removed or it has worn out. It should be noted that the outer seal (3) preferably comprises means, such as small tab or flap, that allow said outer seal (3) to be removed manually. Therefore, during the transport and/or storage of the disposable capsule (1), said outer seal (3) may wear out due to rubbing against a foreign element, accidentally removing the outer seal (3) from the disposable capsule (1). In this case, the existence of an internal seal (2) guarantees that the medicament is kept sealed inside the disposable capsule (1).

In those cases in which there is more than one internal seal (2), the internal seals (2) located further inside the disposable capsule (1) have the purpose of separating the different phases in which the medicament may be stored inside the disposable capsule (1). Said phases may comprise liquid phases or a combination of liquid and solid phases.

There is also the possibility (not represented in the drawings) that the disposable capsule (1) does not comprise any internal seals (2), and that it comprises a single outer seal (3) that has the purpose of protecting the medicament inside the disposable capsule (1) from the environment.

The nebuliser (4) may form a single body with the disposable capsule (1) of the nebuliser device, so that both the nebuliser (4) and the disposable capsule (1) are disposed of once the dose of the medicament contained inside the disposable capsule (1) has been used.

Alternatively (and preferably), the nebuliser (4) can be removed from the disposable capsule (1) once the dose of the medicament contained inside the disposable capsule (1) has been used.

In this way, the nebuliser (4) can be reused, resulting in savings in materials and costs for users since they do not have to acquire a new nebuliser (4) each time the nebuliser device is used, and they do not need to clean the disposable capsule (1) after using the nebuliser device; they just need to clean and disinfect the nebuliser (4) after using it, and they only need to purchase disposable capsules (1) at the chemist or hospital, which are coupled to the nebuliser (4) in order to administer the right medicament.

Figure 1A:
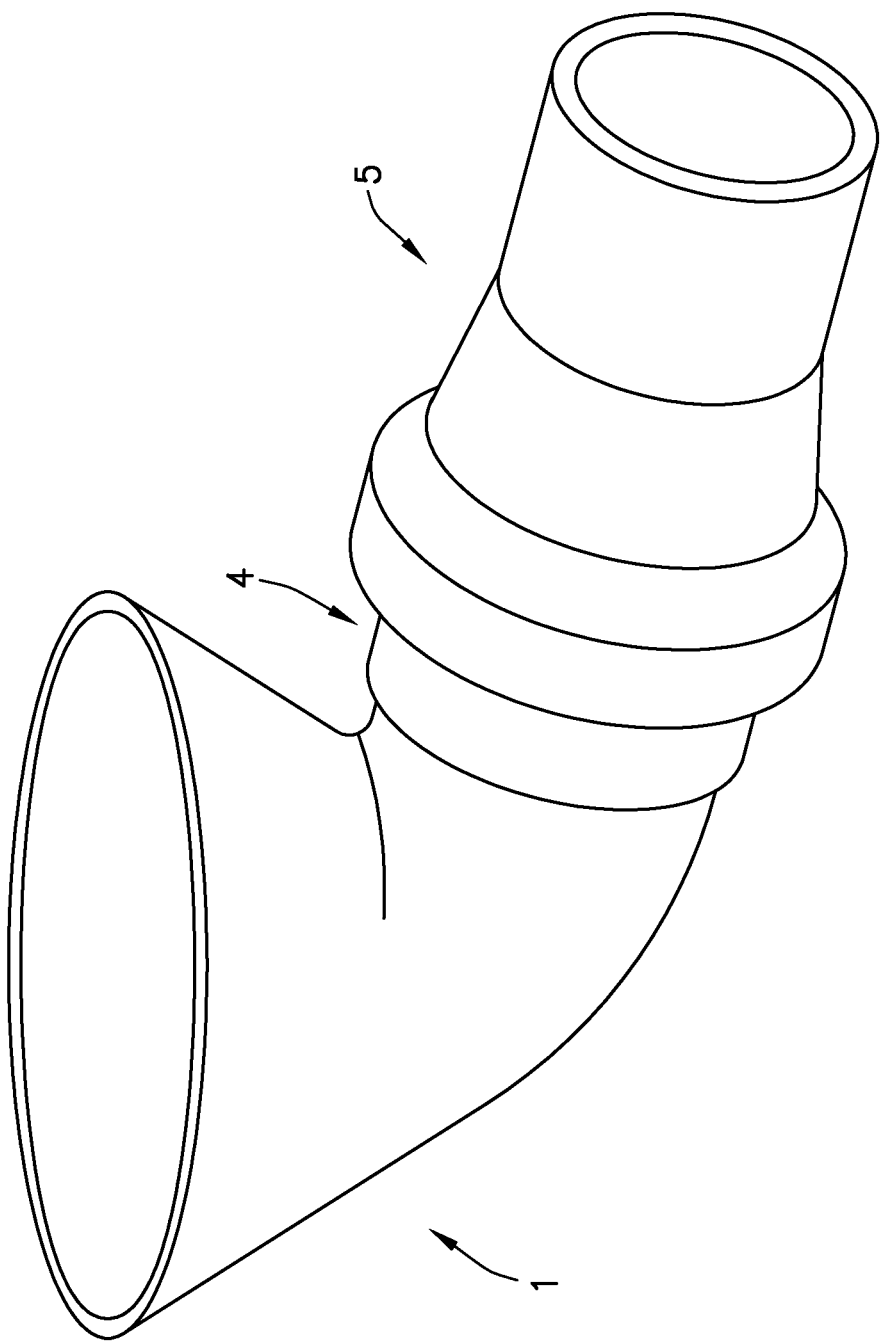
FIG. 1A: Shows a perspective view of an embodiment of a nebuliser device in which the disposable cartridge, nebuliser, and nozzle of the device form part of a single body.

The nozzle (5) may also form part of a single body with the nebuliser (4) and/or with the disposable capsule (1) and/or the casing (10), or alternatively (and preferably), it may be an independent body from the others, which is coupled to the nebuliser (4) and/or the disposable capsule (1) and/or the casing (10) in order to administer the medicament each time the nebuliser device is used, so that after the medicament has been applied the parts that make up the nebuliser device are separated, the empty disposable capsule (1) is disposed of, and the nozzle (5) and the nebuliser (4) are disinfected and cleaned. The nebuliser device with the disposable capsule (1), nebuliser (4), and nozzle (5) forming part of a single body is shown in FIG. 1A.

According to a preferred use of the nebuliser device, users could hand over the nebuliser (4) of their nebuliser devices to a company specialised in sanitary services, so that said company is the one in charge of cleaning and disinfecting the nebuliser (4).

In this way, users save time since they do not need to personally clean the nebuliser (4) of their nebuliser device, since said cleaning and disinfecting operation is carried out by a professional or a company that provides specialised sanitary services.

In order to correctly administer the medicament each time the nebuliser device is used, the user purchases a disposable capsule (1) that contains the right medicament in the right dose for each case, and then couples the nebuliser (4) to the lower cylindrical part of the disposable capsule (1).

The punch (6) of the nebuliser (4) perforates both the outer seal (3) on the lower part of the disposable capsule (1) (when it has not been removed manually), as well as each internal seal (2) of said disposable capsule (1) (in those embodiments in which the disposable capsule (1) comprises at least one internal seal (2)). In this way, the different phases in which the medicament may be stored separately inside the disposable capsule (1) are mixed, and afterwards the mixture of the medicaments flows through the inside of the punch (6) towards the mesh (8) that is actuated by the piezoelectric device (7). In order to do so, the punch (6) has a hollow geometry with a cutting edge.

Figure 2:
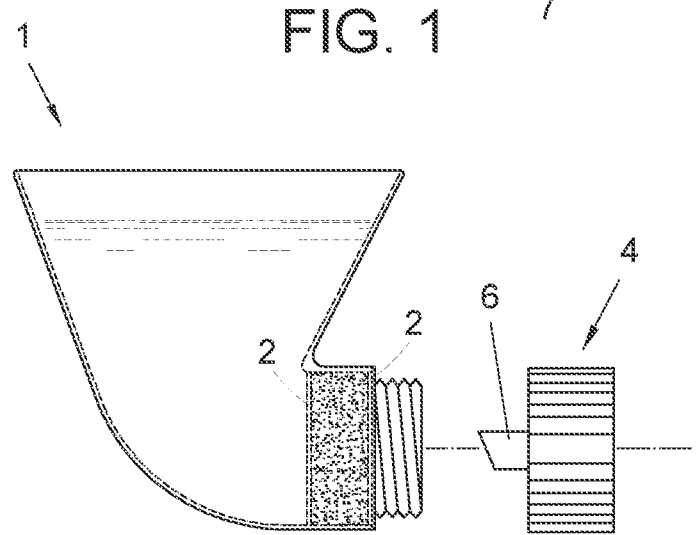
FIG. 2: Shows a cross-section view of a second variation of the first embodiment of the nebuliser device.
Figure 3:
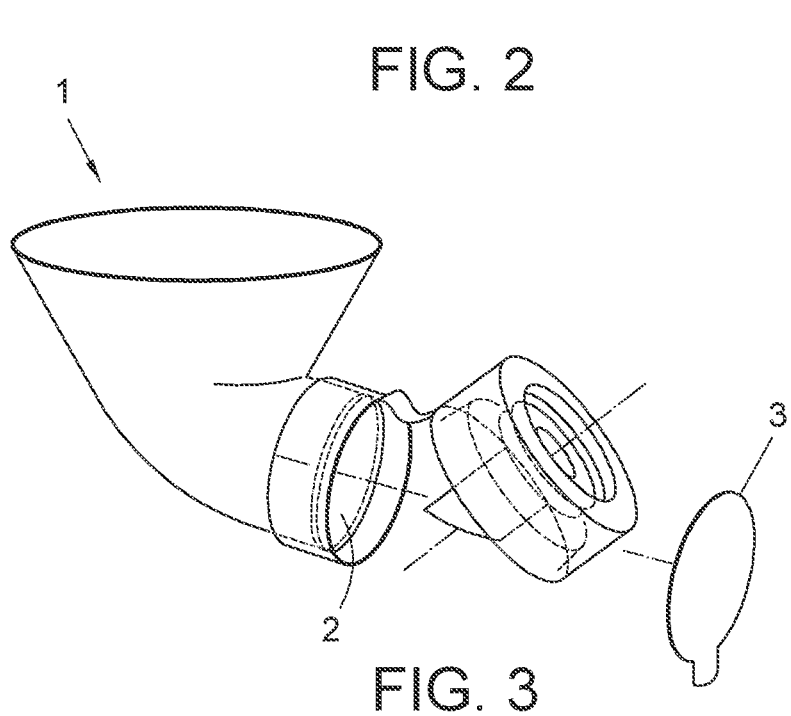
FIG. 3: Shows a cross-section view of a third variation of the first embodiment of the nebuliser device.

FIGS. 1, 2, and 3, represent different variations of the first embodiment of the nebuliser device. Said drawings show the main components of the nebuliser device, and they do not represent the casing (10).

The variations shown in FIGS. 1, 2 and 3 only differ in the way the nebuliser (4) and the disposable capsule (1) are coupled together.

The coupling between the nebuliser (4) and the disposable capsule (1) is preferably done by threaded means (see FIG. 2). Alternatively (see FIG. 3), the nebuliser (4) may be coupled by means of swivelling to the disposable capsule (1), so that it turns by means of a hinge and is coupled by means of pressure fitting to said disposable capsule (1).

The mesh (8) of the nebuliser (4) is actuated by the piezoelectric device (7), preferably by means of pushing a switch, button or another means of activating/deactivating (9) the device, comprised in the casing (10) of the nebuliser device.

The piezoelectric device (7) actuates the vibrating mesh (8) causing the mesh (8) to vibrate at a high frequency vibration (~180 kHz).

It may also be necessary to shake the disposable capsule (1) before the medicament is administered in order to help the medicament to mix and homogenise correctly.

The nozzle (5) may be disposed of (if it is an independent body from the rest of the components of the device) after each use, or it may be reused.

FIG. 1 shows the nozzle (5) as an independent body from the rest of the components of the device; in this case, the nozzle (5) is coupled to the nebuliser (4) and to the disposable capsule (1). Said coupling can be done by threaded means, by means of an existing thread on the end of the nozzle (5) that is coupled to the rest of the nebuliser device, with the nozzle (5) tightening either to the nebuliser (4) or to the disposable capsule (1).

Alternatively, the coupling between the nozzle (5) and the rest of the nebuliser device may be carried out by other means different from threaded coupling, such as for example, by pressure fitting.

Alternatively, the nozzle (5) can be coupled to the casing (10) of the nebuliser device, according to the coupling means described above.

Figure 4:
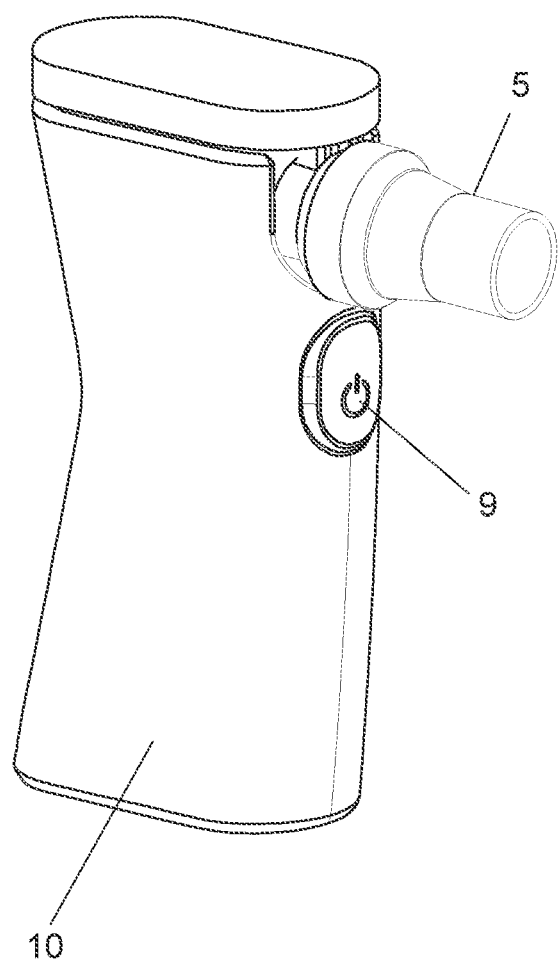
FIG. 4: Shows a perspective view of a first type of casing of the nebuliser device, in which the main components of the nebuliser device that is the object of the invention are integrated together.

FIG. 4 shows a first type of casing (10) of the nebuliser device, in which the main components of the nebuliser device that is the object of the invention are integrated together. The casing (10) of the nebuliser device comprises means for activating/deactivating (9) the device, such as a button, which when it is pushed it causes the piezoelectric device (7) of the nebuliser (4) to actuate the vibrating mesh (8) in order to correctly apply the medicament.

Figure 5:
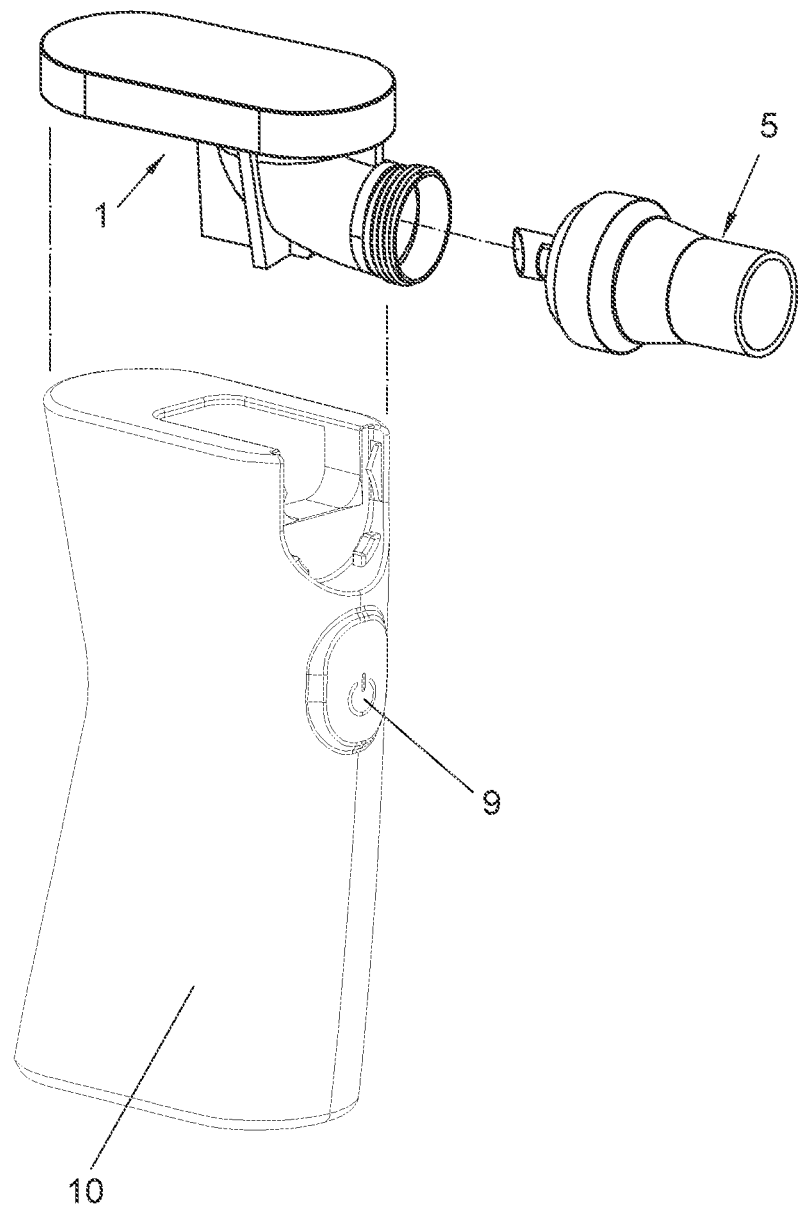
FIG. 5: Shows a perspective view of the assembly of the main components of the nebuliser device that is the object of the invention, in the casing shown in FIG. 4.

FIG. 5 shows a perspective view of the assembly of the main components of the nebuliser device that is the object of the invention, in the casing (10) shown in the previous figure.

Figure 6:
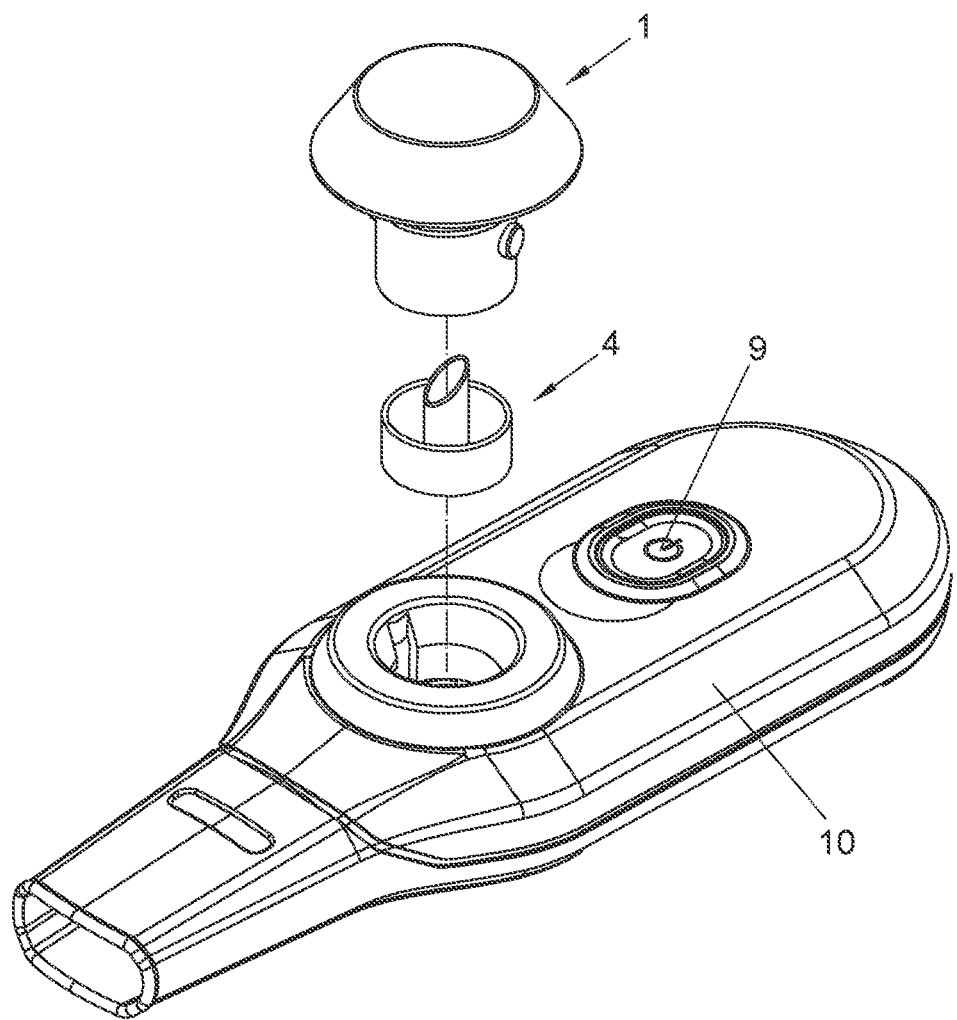
FIG. 6: Shows a perspective view of the assembly of a second embodiment of the nebuliser device, in a second type of casing.

FIG. 6 shows a perspective view of the assembly of the main components of the nebuliser device (according to a second embodiment of said nebuliser device), in a second type of casing (10).

In said second embodiment of the nebuliser device shown in FIG. 6, the disposable capsule (1) does not have an L-shaped geometry and it comprises an upper part preferably in the shape of a vertical cone and a lower part in the shape of a vertical cylinder, which is inserted in the casing (10) of the nebuliser device, that in this case forms a single body with the nozzle (5).

When the disposable capsule (1) is inserted in the nebuliser device, the punch (6) of the nebuliser (4) perforates an internal seal (2) of the disposable capsule (1), gaining access to the medicament contained inside said disposable capsule (1).

As the means of activating/deactivating (9) the device are pushed, such as a button located on the casing (10) of the nebuliser device, the piezoelectric device (7) of the nebuliser (4) is activated, which in turn actuates the vibrating mesh (8).

The invention claimed is:

1. A nebulizer device for administering medicaments, comprising:
   a casing,
   a nozzle,
   a nebulizer configured to be arranged in the casing, and
   a disposable capsule, the disposable capsule forming a chamber that houses a liquid medicament, and forming an independent body that can be inserted into the casing, wherein the nebulizer comprises a piezoelectric device and a vibrating mesh actuated by the piezoelectric device, and a punch with a cutting geometry on an end thereof configured to perforate an outer seal or inner seal of the disposable capsule when the disposable capsule is inserted into the casing, and wherein the punch is hollow to allow the liquid medicament in the chamber to flow through the punch towards the mesh of the nebulizer.

2. The nebulizer device according to claim 1, wherein the casing comprises a switch or a button for selectively activating the piezoelectric device that actuates the vibrating mesh of the nebulizer.

3. The nebulizer device according to claim 1, wherein the nozzle forms an integral part of the casing.

4. The nebulizer device according to claim 1, wherein the disposable capsule comprises an outer seal protecting the medicament housed therein.

5. The nebulizer device according to claim 1, wherein the disposable capsule comprises at least one internal seal protecting the medicament housed therein and/or separating different phases of the medicament housed therein.

6. The nebulizer device according to claim 5, wherein the medicaments housed inside the disposable capsule comprise at least two different phases selected between:
  a. liquid phases; and
  b. a combination of liquid and solid phases,
  wherein each of said phases is located on different sides of the internal seal.

7. The nebulizer device according to claim 1, wherein the disposable capsule comprises an upper part in the shape of a vertical cone and a lower part in the form of a cylinder.

8. The nebulizer device according to claim 1, wherein the disposable capsule comprises an L-shaped geometry with a vertical cone in an upper part thereof, and an oblique or horizontal cylinder in a lower part thereof.

9. A nebulizer device for administering medicaments, comprising:
  A casing,
  a nozzle, and
  a nebulizer,
  wherein the nebulizer comprises a piezoelectric device and a vibrating mesh actuated by the piezoelectric device, and the nebulizer device further comprises a punch with a cutting geometry on an end thereof configured to perforate an outer seal of a disposable capsule which houses a liquid medicament, and forms an independent body that can be inserted into the casing, and wherein the punch perforates the outer seal of the disposable capsule when the disposable capsule is inserted into the casing, wherein the punch is hollow to allow the liquid medicament of the disposable capsule to flow through the punch towards the mesh of the nebulizer.

10. The nebulizer device according to claim 9, wherein the nozzle forms an integral part of the casing.

11. The nebulizer device according to claim 9, wherein the casing comprises a switch or a button for selectively activating the piezoelectric device that actuates the vibrating mesh of the nebulizer.

12. A nebulizer device for administering medicaments, comprising:
  a casing,
  a nozzle, and
  a nebulizer, wherein the nebulizer comprises a piezoelectric device and a vibrating mesh actuated by the piezoelectric device,
  wherein the casing is configured to receive a disposable capsule housing a liquid medicament, and the nebulizer device further comprises a hollow punch with a cutting geometry on an end thereof such that the hollow punch perforates an outer seal of the disposable capsule when the capsule is inserted into the casing, and the liquid medicament of the disposable capsule flows through the punch towards the mesh of the nebulizer when the disposable capsule is coupled to the casing.

\* \* \* \* \*